United States Patent [19]

Kozlov et al.

[11] Patent Number: 4,806,862

[45] Date of Patent: Feb. 21, 1989

[54] METHOD OF MAGNETOGRAPHIC INSPECTION OF QUALITY OF MATERIALS

[75] Inventors: Valery S. Kozlov; Elena A. Polyakova; Alexei E. Novikov, all of Minsk; Mikhail T. Krupko, Kolomna, all of U.S.S.R.

[73] Assignee: Belorussky Politeknichesky Institute, Minsk, U.S.S.R.

[21] Appl. No.: 895,192

[22] Filed: Aug. 11, 1986

[51] Int. Cl.$^4$ .................. G01N 27/85; G01R 33/12
[52] U.S. Cl. ........................... 324/213; 324/228
[58] Field of Search .................. 324/213–216, 324/228

[56] References Cited

U.S. PATENT DOCUMENTS

| | | | |
|---|---|---|---|
| 3,341,771 | 9/1967 | Crouch et al. | |
| 3,430,133 | 2/1969 | Greiner et al. | 324/213 |
| 4,447,778 | 5/1984 | Stumm | 324/213 |

FOREIGN PATENT DOCUMENTS

| | | |
|---|---|---|
| 2253688 | 3/1977 | Fed. Rep. of Germany . |
| 315112 | 10/1971 | U.S.S.R. . |
| 564583 | 9/1977 | U.S.S.R. . |

*Primary Examiner*—Gerard R. Strecker
*Attorney, Agent, or Firm*—Lilling & Greenspan

[57] ABSTRACT

A method of magnetographic quality inspection of a material, whereby a magnetic-recording medium is applied onto the material to be inspected, and they are together magnetized so that the resulting magnetogram can be used to assess the quality of the material. According to the invention, the intensity of the magnetizing field is established by the maximum curvature of the surface of a drop of a magnetic fluid applied onto the surface of the material to be inspected. A magnetic substance is placed between the magnetic-recording medium and the material so that the surface of the latter is smoothed out. A magnetizing device comprising a magnetic yoke and a magnetizing coil lossely fitted thereon and composed of sections which are connected in parallel to one another.

2 Claims, 1 Drawing Sheet

METHOD OF MAGNETOGRAPHIC INSPECTION OF QUALITY OF MATERIALS

BACKGROUND OF THE INVENTION

1. Field of the Invention

This invention relates to test instruments and, in particular, to a method of magnetographic inspection of the quality of materials and a device therefor. It is designed to provide magnetic recording of flaw fields in the process of magnetographic flaw detection, for example, during quality testing of ferrogmagnetic products, welded joints or quality inspection of their parts.

2. Description of the Prior Art

Known in the art are quality tewt magnetographic methods and devices realizing these methods (cf., for example, U.S. Pat. No. 3,341,771), wherein a magnetizing medium is applied on a test material, and they are both magnetized. To this end, a magnetizing coil installed in the central portion of a magnetizing yoke is connected to a magnetizing current source, and flaw leakage fields are recorded on a magnetic-recording medium which is in contact with the surface of the material. The information contained in the recorded magnetogram is the evidence of the quality of the tested material and the extent location of flaws.

But this prior art method is deficient in that the inspection is not reliable because the leakage fields of flaws are recorded against the background of interferences caused by irregularities of the surface of the tested material. The level of such interference often exceeds the useful signal magnitude. In addition, this testing method cannot provide the desired intimate contact between the magnetic-recording medium and the surface of the tested material, which adds to the inaccurateness of the inspection data.

Also known in the art is a method for magnetographic flaw detection in ferromagnetic products (cf., for example, FRG Pat. No. 2,253,688, IPC G 01 N), wherein a temporary self-sustaining contact is achieved between the magnetic tape and the surface of the test zone on a product. To this end, adhesion between one side of the magnetic tape and said surface is attained by means of a self-adhesive magnetic tape having one or two additional layers of adhesive and suitable for subsequent electronic read-out. In this case, an intimate contact of the magnetic tape medium and the test zone on the product surface is ensured.

But this method is not free of disadvantages which consist in lower efficiency of testing and inconveniences due to additional technological operations involving application of talcum powder onto the additional adhesive layer or selective dissolution of the adhesive coating, which is necessary to neutralize the adhesive coating after the recording is completed and before the read-out of this recording in an electronic reader.

One more disadvantage of this method consists in that the technique of obtaining information on the product quality becomes more complicated. It involves application of additional, e.g. PVC, films to protect accidental adhesion of the magnetic tape. Such tape is inconvenient in application from a roll equipped with an unrolling device. In addition, when the surface of the tested material is irregular and has sharp angles and thicknesses, the level of interferences is still often higher than the level of the useful signal, which is a serious deficiency of this method.

Also known in the art is a method of magnetographic inspection of welded joints (cf., USSR Inventor's Certificate No. 564,583, IPC G 01 N 27/82, published in "Biulleten Izobreteny" No. 25, 1975), wherein the tested product and a magnetic-recording medium applied over the welded seam are magnetized together by the static and alternating magnetic fields. The tested member and the tape are magnetized in succession by the static and alternating magnetic fields whose directions are opposite.

Also known in the art is a magnetizing device to realize this method of magnetographic inspection (cf., for example, USSR Inventor's Certificate No. 315,112, IPC G 01 N 27/82, 1969), which comprises a magnetic core and a magnetizing coil placed in the central portion of said core, the coil being connected to a magnetizing current source, and a clamping plate on which a recording medium is placed. A two-position holding lock is provided for the clamping plate carrying the magnetic recording medium in this magnetizing device in order to improve the sensitivity of the magnetographic inspection and to reduce the interferences caused by the reinforcement bead of the welded seam.

The prior art methods and devices do not provide a uniform magnetic flux in the test zone if the test object has bulges and surface irregularities. They also offer no means for assessment and compensation of the effect of air gaps due to loose and dissimilar mating of the poles of the magnetizing device to the object, which is often the case in practical applications. Unstable magnetic contact is also often the reason of inaccurate assessment of the quality of the tested material.

SUMMARY OF THE INVENTION

The primary object of this invention is to provide a method of magnetographic quality inspection of material, which ensures high reliability of information about the quality of the material of complex shaped test objects.

Another object of the invention is to provide a method of magnetographic quality inspection of complex shaped test objects, including those having bulges on the surface of the test zone, the access to the objects being possible only from one side.

Yet another object of the invention is to provide a method of magnetiographic quality inspection of material, which can substantially improve the quality of inspection in cases when irregularities or errors are introduced by, for example, the welding process.

Still another object of the invention is to provide a method for magnetographic quality inspection of complex shaped objects in adverse conditions, e.g. under water and in not easily accessible places, the process of producing magnetograms being made simpler, and their interpretation also simpler and faster.

A further object of the invention is to improve the efficiency and quality of testing, and at the same time keep the cost of the proposed technical solutions sufficiently low, and also see to it that testing does not require skilled personnel.

One more primary object of the invention is to provide a device for magnetizing the material being inspected, which can supply reliable information about the quality of complex shaped objects which have bulges in the test zone, including, for example, welded joints featuring reinforcement beads along the seam.

These and other objects are achieved in that in a method of magnetographic quality inspection of a material, comprising the steps of a magnetic-recording medium is applied onto the material to be inspected, and they are together magnetized in order to obtain on the magnetic-recording medium, a magnetogram which can be used to access the quality of the tested material after it is interpreted, according to the invention, a magnetic fluid is applied onto the surface of the material to be inspected prior to other operations, the intensity of the mangnetizing field by which the maximum curvature of the liquid surface is achieved is registered, a magnetic substance is then placed between the magnetic-recording medium and the material in order to smooth out the surface of this material, and then they are magnetized by a field having the registered intensity.

This permits obtaining much mroe reliable information about the quality of test objects having complex shapes, and simpler tehcnique of obtaining such information.

Advisably, a magnetic substance composed of ferrogmagnetic particles distributed in an adhesive medium should be used in order to make the method more convenient and improve the test efficiency in adverse conditions.

These and other objects are achieved by a magnetizing device, realizing the method of magnetograpic inspection of the quality of a material, comprising a magnetic yoke, and a magnetizing coil installed in the central portion of said magnetic yoke, which is connected to a magnetizing current source. According to the invention, the magnetizing coil should advisably be made of separate sections connected to one another in parallel and fit loosely on said magnetic yoke.

Advantageously, the number of turns in each section of the magnetizing coil should correspond to the thickness of the material in the particular area where this coil section is located on the test object in order to achieve a more uniform magnetic flux in the test zone irrespective of the varying thickness of the test object, e.g. the reinforcement of the weld.

This makes the information recorded in the process of magnetization more reliable and the assessment of the size of flaws in such objects more accurate.

BRIEF DESCRIPTION OF THE DRAWINGS

The invention will now be described in greater detail with reference to the accompanying drawings, wherein.

DESCRIPTION OF THE PREFERRED EMBODIMENT

The method of magnetographic material quality inspection is described with reference to a specific embodiment concerned with quality inspection of welded joints.

The method of magnetographic inspection of the quality of a material comprises the following steps, according to the invention.

Figure 1:
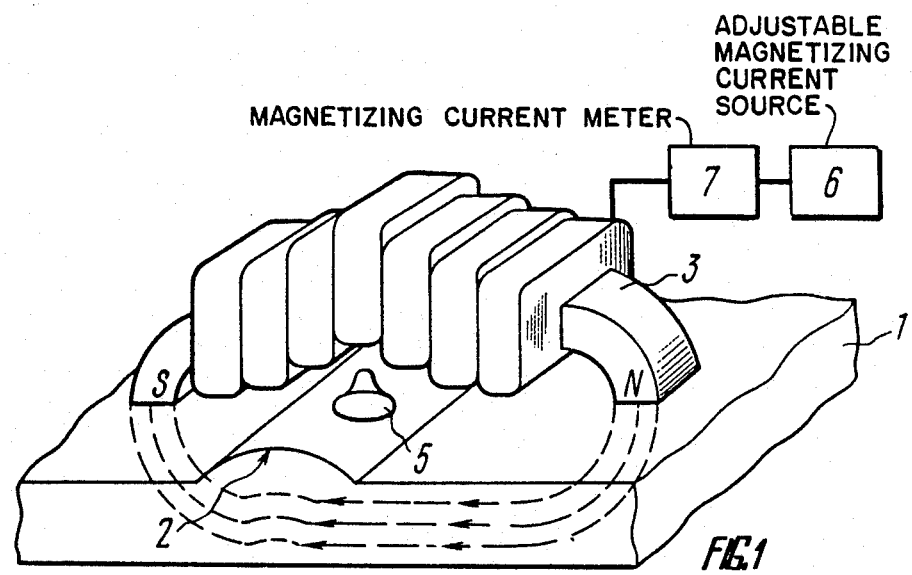
FIG. 1 schematically illustrates a method of magnetographic inspection of the material quality and shows a block diagram of a device realizing this method, according to the invention.

A material (object) 1 (FIG. 1) to be inspected features a test zone 2, for example, a weld. An electromagnet 3 which is the source of the magnetizing field is placed on said material 1. In advance, before a magnetic-recording medium 4 (FIG. 2) is applied onto the test zone 2, a magnetic fluid 5 is applied by dripping on the surface of the material 1 to be inspected in the test zone 2 as shown in FIG. 1. An adjustable source 6 of magnetizing current, which is equipped with a magnetizing current meter 7, is connected to the mains. The intensity of the magnetizing field is varied by adjusting the current in the magnetizing circuit. While this is being done, the curvature of the surface of the magnetic field 5 is watched visually or by optical devices.

When the surface of the magnetic fluid 5 reaches its maximum curvature, the reading of the magnetizing current meter 7 is recorded. The magnetizing current may be measured by any known method. In this manner the optimal test conditions are established in order to ensure its maximum sensitivity by compensating the scattering of the magnetic flux in real test conditions in any portion of the test zone 2 of the object. Air gaps in the magnetizing circuit are due to loose mating of the poles of the electromagnet 3 to the surface of the test zone 2. This is usually because solidified splashes of metal are not removed from the surface of the workpiece or when the surface is "corrugated" in the test zone 2 and under the poles of the electromagnet 3, or when welded plates are shifted or mismatched during welding, etc. The magnetic fluid 5 is used as an indicator of the magnetizing conditions and ensures that a good quality magnetogram is obtained on a particular test zone 2. It can help adjust the magnetizing conditions to accomodate for the negative factors and thus improve the reliability of the quality inspection.

The magnetic fluid 5 can be, for example, a suspension of ferromagnetic particles of a magnetic powder, crocus, in either water or kerosense with an emulsifying agent. The magnetic liquid 5 can also be a colloidal solution of magnetite.

Figure 2:
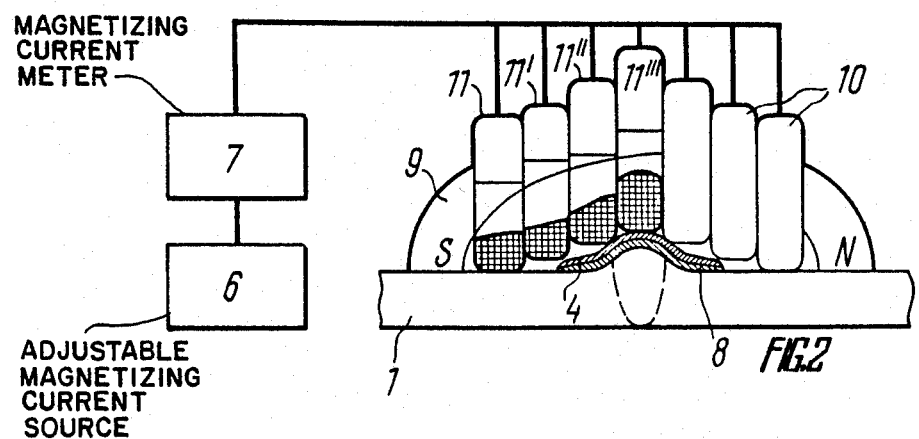
FIG. 2 shows a schematic of a device realizing the method of magnetographic material quality inspection, using a magnetic substance, where for clarity some sections of the magnetizing coil are shown with a quarter torn away, according to the invention.

Referring to FIG. 2, a magnetio substance 8 is applied onto the test zone 2, particularly on the thicker portion of the weld, the bead. This magnetic substance 8 is to smooth the surface to be tested. The magnetic substance 8 is usually a material comprising ferromagnetic particles distributed in an adhesive medium. The adhesive medium ensures adhesion of the magnetic substance 8 to the material 1 to be inspected, and, also, to the magnetic-recording medium 4, that is the magnetic tape, on the test zone 2.

The magnetic substance 8 is applied either manually or by a putty knife. Certain experimentally established recommendations are to be observed to obtain an optimal surface of the magnetic substance. The test zone 2, after it is covered by the magnetic substance 8, should be smooth, the passage from the metal of the object 1 to the reinforcement of the weld 2 being rounded off. The height and width of the reinforcement bead, after the shape thereof is smoothed, is dependent on the geometrical dimensions of the weld itself. In some cases, particularly during mass production, pallets for application and shaping of the magnetic substance 8 are provided with notches of different sizes to fit each particular type of the weld.

The ferromagnetic filling agent whose particles are uniformly distributed in the adhesive binding medium can be composed of particles of a ferromagnetic material having a high saturation flux density, permendur, for example. The adhesive medium which is a liquid emulsifying and binding substnace can be a liquid organosilicate paint.

This magnetic substance has one advantage useful for many practical application—it retains its adhesive properties in water. This is particularly important when such an adhesive magnetic paste is used for quality inspection under water, especially in flowing water, or when test zones are located on the ceiling.

Two problems are resolved at the same time. First, the surface is smoothed out and, thereby the magnetic flux density in the weld area is also evened out. Second, a convenient means is provided to secure the magneticrecording medium with the aid of the adhesive magnetic substance 8. To secure the magnetic tape 4, it is sufficient to place it on the smoothed-out surface of the material to be inspected and roll or press the tape down. This can be easily done by such known devices as a rubber roller (not shown).

The magnetic substance 8 applied onto the surface of the object to be inspected has serious effects on the results of the test. The intensity of the magnetic flux in the weld joint zone depends on the shape of the weld reinforcement, its demagnetizing factor, and irregularities of the weld surface. In consequence, the magnetic field is irregular because of the varying thickness of the material in the weld zone. Without the magnetic substance 8, accurate detection of weld flaws, their classification and sizing are difficult. Or, in other words, the reliability and quality of magnetographic flaw detection depends, in practical terms, on the geometrical dimensions, shape, and conditions of the surface of the weld reinforcement. To reduce the effect of these factors and provide a convenient inspection method, it provided advisable to apply a layer of a magnetic substance 8 to smooth out the surface of the test zone 2.

The magnetic-recording medium 4 is applied on the levelled off surface of the test zone 2 of the material 1, e.g. a weld. Then the contact of the magnetic-recording medium 4 with the surface of the test zone 2 is checked for tightness. The test zone 2 of the material 1 to be inspected, together with the magnetic substance 8 and the magnetic-recording medium 4, are then magnetized by a field of the previously established intensity. To this end, the magnetizing current source 6 is switched on, being previously adjusted to the established optimal rating. The magnetogram obtained on the magnetic tape 4 is later read out by means of known devices. To this end, when the magnetogram is completed and the magnetic-recording medium 4 is removed from the test zone 2 of the object 1, the magnetic tape 4 is cleaned, the adhesive paste just wiped off the tape, which is technologically more convenient and simmpler as compared to applying talcum powder and selective dissolving of the adhesive layer as in other prior art methods.

The magnetizing device realizing the method of the magnetographic quality inspection, according to the invention, comprises a magnetic yoke 9 (FIG. 2), a magnetizing coil 10 installed in the central portion of said yoke 9. The magnetizing coil 10 is connected to the magnetizing current source 6 equipped with a magnetizing current meter 7. The magnetizing coil 10 is composed of sections 11, 11′, 11″, etc. The coil sections 11 are electrically coupled with one another into a parallel circuit, and are placed freely on the magnetic yoke 9, special openings (not shown) being provided in the frames of the coil sections 11 to fit them on the yoke 9. The opening is large enough for the sections to be shifted in the direction perpendicular to the surface of the object being inspected.

The number of coil turns in each section 11, 11′, 11″, 11‴ of the coil 10 corresponds, according to the invention, to the thickness of the material 1 being inspected in the test zone 2 where such a section is located. For example, the number of coil turns in the sections 11 and 11′ adjoining the S pole of the electrtomagnet 3 is less than that of the central sections 11″ and 11‴ positioned on the reinforcement bead of the weld 2 of the object 1. To summarize, the number of coil turns in sections 11 vary in accordance with the experimentally tested principle and depends on the size, height and width of bulges in inspected products.

The magnetizing device realizing the magnetographic quality inspection method, according to the invention, operates as follows.

Magnetographic quality inspection of the material 1 is effected by exciting a magnetic flux in said material 1. To this end, magnetizing current is passed through the coil 10 installed on the magnetic yoke 9 of the electromagnetic 3. THe magnetic lines of force are arranged approximately across the plane of symmetry of the electromagnet 3, e.g. perpendicular to the weld 2. When a flaw is present in the welded joint, e.g. a crack, a pit, etc., some magnetic force lines emerge on the surface during the magnetizing of the test zone 2. A leakage field is produced, which is located in the area of the flaw and above the surface of the tested object. This leakage field is recorded on the magnetic tape 4 which is in contact with the surface of the test zone 2. Known devices (not shown) are used to read and interpret magnetograms obtained in this manner.

The magnetizing device realizing the method of magnetographic quality inspection is placed on the material 1 to be inspected so that the test zone 2, e.g. the weld bead, on which the magnetic-recording medium 4 and the magnetic substance 8 are positioned, is approximately in the center of and symmetrically with the magnetic yoke 3. The sections 11 of the magnetizing coil 11 connected in a parallel circuit are joined to the magnetizing current source 6 via the magnetizing current meter 7, e.g. ammeter. The sections 11 of the magnetizing coil 10 are arranged on the surface of the object 1 to be inspected so that they describe the shape thereof, since these sections 11 can be freely shifted in the plane perpendicular to the plane of the object 1 to be inspected. The magnetogram is obtained by magnetizing the test zone 2 by the magnetic field. whose intensity has been recorded by means of the magnetic liquid 5 as described above. The magnetic field is levelled off in the test zone 2 of the test object having a complex shape. Since the magnetizing coil 10 is located directly on the surface of the test object 1, magnetization of the test zone 2 is of high quality. THe uniformity of the magnetic flux intensity in the test zone 2 where the magnetic-recording medium 4 is located is achieved by providing sections 11 resting on the thicker portion of the welded object 1 with a greater number of turns. This is one more advantage of the magnetizing device according to the invention as contrasted to the conventional position of the magnetizing coil 10 on the magnetic yoke 9 in prior art magnetizing devices.

As the sections 11 of the magnetizing coil 10 are connected in parallel, the magnetizing device also provides for identical recordings on the medium 4 irrespective of the polarity of connection of the magnetizing coil 10 to the magnetizing current source 6.

It is to be understood that the present invention is not limited to the disclosed embodiments and may be variously otherwise embodied within the scope of the appended claims.

The present invention can be used in civil engineering, oil-gas industry for quality inspection of pipes for critical applications in machine building industry to detect defects in rolled products, in shipbuilding industry for quality testing of welds of ship hulls and tanks, and in other fields of industry where the access to products to be tested for continuity defects is possible from one side only.

The method of magnetographic quality inspection of materials and a device realizing said method offer the advantage of a more reliable information about the quality of complex shaped objects, including those with bulged welded joints, e.g. reinforcement beads of welds, and irregularities of the surface of the test zone.

This invention also permits a lower level of interferences, a more reliable isolation of the useful signal when magnetograms are interpreted, and a better analysis of the useful signals, that is better detection of the flaw, its classification, and sizing.

Moreover, the proposed method and device for magnetographic quality inspection provide reliable information even in cases when the tightness of the fit of the poles of the magnetizing device to the surface of the test zone varies while passing from one area to another. This can be caused by unremoved "metal splatter", corrugations, mismatchment of welded surfaces, etc. The reliability is still good because the leakage fields of air gaps are safely compensated. The technique of producing magnetograms is made much simpler, the efficiency of testing is better in complex conditions, e.g. under water, especially in flowing water, or where test zones are on the ceiling. The magnetic tape is convenient to handle in places not easily accessible. The tape is also easier to handle during interpretation and analysis.

What is claimed is:

1. A method of magnetographic quality inspection of a material, comprising the steps of:
   applying, in advance, at least one drop of a magnetic fluid on an area of the surface of said material to be inspected;
   producing a magnetizing field proximate to the area of said material to be inspected to cause at least some magnetic lines to pass through the area of the material to be tested;
   changing the intensity of the magnetizing field and watching the curvature of a surface of said magnetic fluid;
   registering the intensity of the magnetizing field, at which said surface of the drop of the magnetic fluid has the maximum curvature;
   applying a magnetic substance onto the surface of said material to be inspected until the surface of said material is smoothed out;
   applying a magnetic-recording medium on said material to be inspected;
   magnetizing said material to be inspected, said magnetic substance, and said magnetic-recording medium by means of said magnetizing field having the registered intensity;
   obtaining a magnetogram on said magnetic-recording medium; and
   assessing the quality of said material on the basis of said magnetogram.

2. A method of magnetographic inspection of a material, as claimed in claim 1, wherein said magnetic substance is a material comprising ferromagnetic particles distributed in an adhesive medium.

* * * * *